United States Patent [19]

Alder

[11] Patent Number: 5,206,388
[45] Date of Patent: Apr. 27, 1993

[54] PROCESS FOR THE PREPARATION OF 5,6,11,12-TETRATHIOTETRACENE

[75] Inventor: Alex Alder, Arisdorf, Switzerland

[73] Assignee: Ciba-Geigy Corporation, Ardsley, N.Y.

[21] Appl. No.: 872,735

[22] Filed: Apr. 22, 1992

[30] Foreign Application Priority Data

Apr. 25, 1991 [CH] Switzerland ............... 1236/91

[51] Int. Cl.$^5$ .................................... C07D 339/02
[52] U.S. Cl. ............................. 549/31; 549/30
[58] Field of Search ............................. 549/31

[56] References Cited

U.S. PATENT DOCUMENTS

| | | | |
|---|---|---|---|
| 3,636,048 | 1/1972 | Klingsberg | 549/31 |
| 4,981,962 | 1/1991 | Baumann et al. | 548/406 |
| 5,009,812 | 4/1991 | Finter et al. | 524/412 |

OTHER PUBLICATIONS

R. Medne et al, *Chemical Abstracts* 112:178743p, p. 746, abstract of Latv. PSR Zinat. Akad Vestis Khim Ser B, 1989(5) pp. 633-634 (1990).
Latr PSR Zinat. Akat. Vestis, Khim, Ser, p. 633 (1989).
Balodis et al., Chem. Abst. 92(25):215353 (1980).
Haddon et al., Journal of Amer. Chem. Soc. vol. 100 No. 14 pp. 4612-4614 (1978).

*Primary Examiner*—Richard L. Raymond
*Assistant Examiner*—Mark W. Russell
*Attorney, Agent, or Firm*—Kevin T. Mansfield; Edward McC. Roberts

[57] ABSTRACT

The reaction of 5,6,11,12-tetrachlorotetracene with thiourea and sulfur in a polar aprotic solvent yields 5,6,11,12-tetrathiotetracene in high yield and purity. This compound is an electron donor for forming electrically conductive radical cation salts with electron donors.

11 Claims, No Drawings

PROCESS FOR THE PREPARATION OF 5,6,11,12-TETRATHIOTETRACENE

FIELD OF THE INVENTION

The present invention relates to a process for the preparation of 5,6,11,12-tetrathiotetracene by reacting 5,6,11,12-tetrachlorotetracene with a mixture of thiourea and sulfur in a polar aprotic solvent.

DESCRIPTION OF RELATED ART

In Latv. PSR Zinat. Akad. Vestis, Khim. Ser., p. 633 (1989), R. Medne et al. describe the reaction of 5,6,11,12-tetrachlorotetracene with thiourea in hexamethylphosphoric triamide in an inert gas atmosphere. In this reaction, 5,6,11,12-tetrathiotetracene is obtained in moderate yield and in insufficient purity.

SUMMARY OF THE INVENTION

It has now been found that both the yield and the purity of the product can be substantially increased, and that even the inert gas atmosphere can be dispensed with, by the additional and concurrent use of sulfur in this reaction.

DETAILED DESCRIPTION OF THE INVENTION

Accordingly, the invention relates to a process for the preparation of 5,6,11,12-tetrathiotetracene of formula I

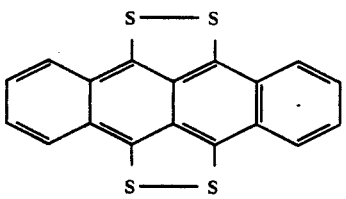

by reacting 5,6,11,12-tetrachlorotetracene of formula II

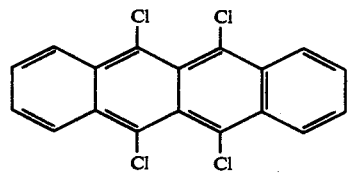

with thiourea in the presence of a polar aprotic solvent, which process comprises carrying out the reaction with a mixture of thiourea and sulfur.

Suitable solvents include N-alkylated acid amides and lactams (typically dimethyl formamide, diethyl formamide, dimethyl acetamide, tetramethylurea, hexamethylphosphoric triamide, N-methylpyrrolidone), ethers (including dipropyl ether, dibutyl ether, tetrahydrofuran, dioxane, ethylene glycol dimethyl or diethyl ether, diethylene glycol dimethyl or diethyl ether), esters and lactones (typically ethyl, propyl or butyl acetate, ethyl propionate, ethyl butyrate, butyrolactone, valerolactone), and sulfones and sulfoxides (typically dimethyl sulfoxide, dimethyl sulfone, tetramethylenesulfone). Preferred solvents are N-alkylated carboxamides and lactams. Dimethyl acetamide is especially preferred.

The reaction temperature may be in the range from 70° to 250° C., preferably from 80° to 200° C. and, most preferably, from 80° to 160° C. In a preferred embodiment of the invention, the reaction is initially carried out for up to 20 hours, preferably for up to 10 hours, at a temperature in the range from 70° to 120° C., preferably from 80° to 110° C., and thereafter for up to 6 hours, preferably for up to 4 hours, at a temperature in the range from more than 120° C. up to 250° C., preferably from 130° C. up to 200° C., most preferably from 130° C. up to 160° C.

The thiourea and the sulfur can be used in equivalent amounts, based on the 5,6,11,12-tetrachlorotetracene. It is preferred to use an excess of thiourea. A preferred embodiment of the novel process comprises using 4.2 to 42 molar equivalents, preferably 10 to 15 molar equivalents, of thiourea, and 2.5 to 10 molar equivalents, preferably 4 to 6 molar equivalents, of sulfur, based on 1 mol of 5,6,11,12-tetrachlorotetracene.

The concentration of 5,6,11,12-tetrachlorotetracene in the reaction mixture is conveniently from 0.01 to 0.20 mol per liter, preferably from 0.06 to 0.12 mol per liter, of solvent.

The reaction can be carried out under elevated pressure, but normal pressure is expedient. It is also possible to carry out the reaction in an inert gas atmosphere. A particular advantage of the novel process is, however, that an inert gas atmosphere is not necessary and that the reaction can be carried out in air.

The novel process can be conveniently carried out by adding the sulfur to the solvent and heating the mixture. Then the thiourea and the 5,6,11,12-tetrachlorotetracene are added to the hot solution, which is stirred for a time at the given temperature. The temperature is thereafter raised and stirring is continued for a time.

The 5,6,11,12-tetrathiotetracene is isolated in a manner known per se, typically by hydrolysing the reaction mixture with a dilute mineral acid, whereupon the product precipitates and can be collected by filtration. The product can be further purified by washing off with a non-solvent, by recrystallisation or by sublimation. Simple washing off alone permits the product to be obtained in high purity.

5,6,11,12-Tetrathiotetracene is a known electron donor which forms with electron acceptors, for example halogens, electrically conductive radical cation salts (organometals) which can be used for providing plastics with an antistatic finish, or as electrodes.

The invention is illustrated by the following Example.

EXAMPLE 6 g of sulfur and 225 ml of dimethyl acetamide are heated to 90° C. in an open vessel. Then 30 g of thiourea are added to the stirred solution, followed by the addition of 13.5 g of 5,6,11,12-tetrachlorotetracene. The reaction mixture is stirred initially for 6 hours at 90° C. and then for 2 hours at 140° C. The black-green solution is cooled to 100° C. and 1125 ml of water which contains 4.5 ml of 5N HCl are added dropwise over 10 minutes. The precipitate is isolated by filtration at 40° C. and washed with 1 liter of water, 1 liter of ethanol, 1 liter of benzene and 200 ml of diethyl ether. The product is then dried at room temperature under vacuum, giving 11.3 g (85% of theory) of 5,6,11,12-tetrathiotetracene in greater than 98% purity.

What is claimed is:

1. A process for the preparation of 5,6,11,12-tetrathiotetracene of formula I

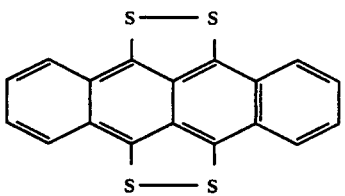

by reacting 5,6,11,12-tetrachlorotetracene of formula II

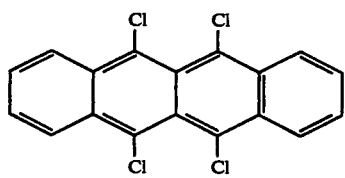

with thiourea in the presence of a polar aprotic solvent, which process comprises carrying out the reaction with a mixture of thiourea and sulfur.

2. A process according to claim 1, wherein the solvent is a N-alkylated carboxamide or a lactam.

3. A process according to claim 2, wherein the solvent is dimethyl acetamide.

4. A process according to claim 1, wherein the reaction temperature is in the range from 70° to 250° C.

5. A process according to claim 1, wherein the reaction temperature is in the range from 80° to 200° C.

6. A process according to claim 1, wherein the reaction is carried out initially for up to 20 hours at a temperature in the range from 70° to 120° C., and thereafter for up to 6 hours at a temperature in the range from more than 120° C. up to 250° C.

7. A process according to claim 6, wherein the reaction is carried out initially for up to 20 hours at a temperature in the range from 80° to 110° C., and thereafter for up to 6 hours at a temperature in the range from more than 130° C. up to 200° C.

8. A process according to claim 1, which comprises using 4.2 to 42 molar equivalents of thiourea and 2.5 to 10 molar equivalents of sulfur per mol of 5,6,11,12-tetrachlorotetracene.

9. A process according to claim 8, which comprises using 10 to 15 molar equivalents of thiourea and 4 to 6 molar equivalents of sulfur per mol of 5,6,11,12-tetrachlorotetracene.

10. A process according to claim 8, wherein the concentration of 5,6,11,12-tetrachlorotetracene in the reaction mixture is from 0.01 to 0.20 mol per liter of solvent.

11. A process according to claim 1, which is carried out in the absence of an inert gas atmosphere.

* * * * *